(12) United States Patent
Olson et al.

(10) Patent No.: US 10,987,490 B2
(45) Date of Patent: Apr. 27, 2021

(54) MULTI-PLANAR STEERABLE MEDICAL SHAFTS

(71) Applicant: ST. JUDE MEDICAL, CARDIOLOGY DIVISION, INC., St. Paul, MN (US)

(72) Inventors: Gregory K. Olson, Elk River, MN (US); Troy T. Tegg, Elk River, MN (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 96 days.

(21) Appl. No.: 16/311,571

(22) PCT Filed: Jun. 20, 2017

(86) PCT No.: PCT/US2017/038276
§ 371 (c)(1),
(2) Date: Dec. 19, 2018

(87) PCT Pub. No.: WO2017/223053
PCT Pub. Date: Dec. 28, 2017

(65) Prior Publication Data
US 2019/0192820 A1 Jun. 27, 2019

Related U.S. Application Data

(60) Provisional application No. 62/352,216, filed on Jun. 20, 2016.

(51) Int. Cl.
*A61M 25/01* (2006.01)
*A61M 25/00* (2006.01)
*A61B 1/005* (2006.01)

(52) U.S. Cl.
CPC .... *A61M 25/0147* (2013.01); *A61M 25/0043* (2013.01); *A61M 25/0136* (2013.01); *A61B 1/0051* (2013.01)

(58) Field of Classification Search
CPC ............ A61B 1/0051; A61M 25/0136; A61M 25/0147
See application file for complete search history.

(56) References Cited

U.S. PATENT DOCUMENTS

2007/0299424 A1* 12/2007 Cumming ......... A61M 25/0012
604/527
2008/0287741 A1 11/2008 Ostrovsky et al.
(Continued)

FOREIGN PATENT DOCUMENTS

CA 2895714 A1 3/2016
WO 914494 A2 7/1994
(Continued)

OTHER PUBLICATIONS

International Search Report and Written Opinion issued in PCT/US2017/038276, dated Sep. 29, 2017 11 pages.

*Primary Examiner* — Deanna K Hall
(74) *Attorney, Agent, or Firm* — Armstrong Teasdale LLP

(57) ABSTRACT

A steerable introducer has a proximal end and a distal end, and includes a steerable sheath having a proximal end and a distal end. The steerable sheath includes an outer layer extending from the proximal end to the distal end of the steerable sheath, and an inner liner disposed within the outer layer and extending from the proximal end to the distal end of the steerable sheath. A first pair of pull wires is disposed between the inner liner and the outer layer, and extends from the proximal end to the distal end of the steerable sheath. A second pair of pull wires is disposed between the inner liner
(Continued)

and the outer layer and extends from the proximal end to the distal end of the steerable sheath.

11 Claims, 9 Drawing Sheets

(56) References Cited

U.S. PATENT DOCUMENTS

| | | |
|---|---|---|
| 2009/0062602 A1 | 3/2009 | Rosenberg et al. |
| 2010/0168717 A1 | 7/2010 | Grasse et al. |
| 2010/0314031 A1 | 12/2010 | Heideman et al. |
| 2012/0010490 A1* | 1/2012 | Kauphusman ......... A61N 1/056 600/373 |
| 2012/0184901 A1 | 7/2012 | Nguyen et al. |
| 2016/0074625 A1 | 3/2016 | Furnish et al. |
| 2016/0096004 A1 | 4/2016 | Gerrans et al. |

FOREIGN PATENT DOCUMENTS

| | | |
|---|---|---|
| WO | 2012068505 A1 | 5/2012 |
| WO | 20140153275 A1 | 9/2014 |

* cited by examiner

MULTI-PLANAR STEERABLE MEDICAL SHAFTS

CROSS-REFERENCE TO RELATED APPLICATIONS

This application is the national stage entry of PCT/US2017/038276, filed on Jun. 20, 2017, which claims the benefit of U.S. Provisional Patent Application No. 62/352,216, filed Jun. 20, 2016, the content of which are hereby incorporated by reference herein in their entirety.

FIELD OF THE DISCLOSURE

The present disclosure relates to steerable medical shafts and methods of making and using steerable medical shafts. More particularly, the present disclosure relates to multi-planar steerable medical shafts and methods of making and using such shafts.

BACKGROUND

Steerable medical shafts such as steerable introducers are often used for the delivery of medical devices, such as catheters, to a target site. Typically, the sheath of the steerable introducer is manipulated through the patient's vasculature and to the intended site, for example, a site within the patient's heart or other organ, with a medical device, such as a catheter, within a lumen of the sheath. The medical device, or a portion thereof, is advanced out of the sheath for use at the target site.

Steerable sheaths for steerable introducers are typically steered in a single plane by use of a pair of pull wires embedded in the sheath on opposite sides of the sheath. In some known sheaths, the pull wires extend parallel to each other in a straight line from a proximal end of the sheath near the handle of the steerable introducer to a distal end of the sheath. The pull wires are fixedly coupled to the sheath at the distal end of the sheath. Pulling one of the pull wires toward the proximal end of the sheath shortens that pull wire, causing a deflectable portion of the distal end of the sheath to deflect within a single plane in the direction of the shortened wire. Pulling the other pull wire toward the proximal end of the sheath shortens the other pull wire, causing the deflectable portion of the distal end of the sheath to deflect within the same plane in the direction of the shortened wire.

SUMMARY OF THE DISCLOSURE

The present disclosure is directed to a steerable introducer having a proximal end and a distal end. The steerable introducer includes a steerable sheath having a proximal end and a distal end. The steerable sheath includes an outer layer extending from the proximal end to the distal end of the steerable sheath, and an inner liner disposed within the outer layer and extending from the proximal end to the distal end of the steerable sheath. A first pair of pull wires is disposed between the inner liner and the outer layer, and extends from the proximal end to the distal end of the steerable sheath. A second pair of pull wires is disposed between the inner liner and the outer layer and extends from the proximal end to the distal end of the steerable sheath.

The present disclosure is also directed to a method of producing a steerable introducer. The method includes positioning a first pair of pull wires adjacent an inner liner of a steerable sheath and positioning a second pair of pull wires adjacent the inner liner of the steerable sheath. The first pair of pull wires extends from a proximal end of the steerable sheath to a distal end of the steerable sheath. The second pair of pull wires extends from the proximal end of the steerable sheath to the distal end of the steerable sheath.

The foregoing and other aspects, features, details, utilities, and advantages of the present disclosure will be apparent from reading the following description and claims, and from reviewing the accompanying drawings.

DETAILED DESCRIPTION OF THE DISCLOSURE

Figure 1:
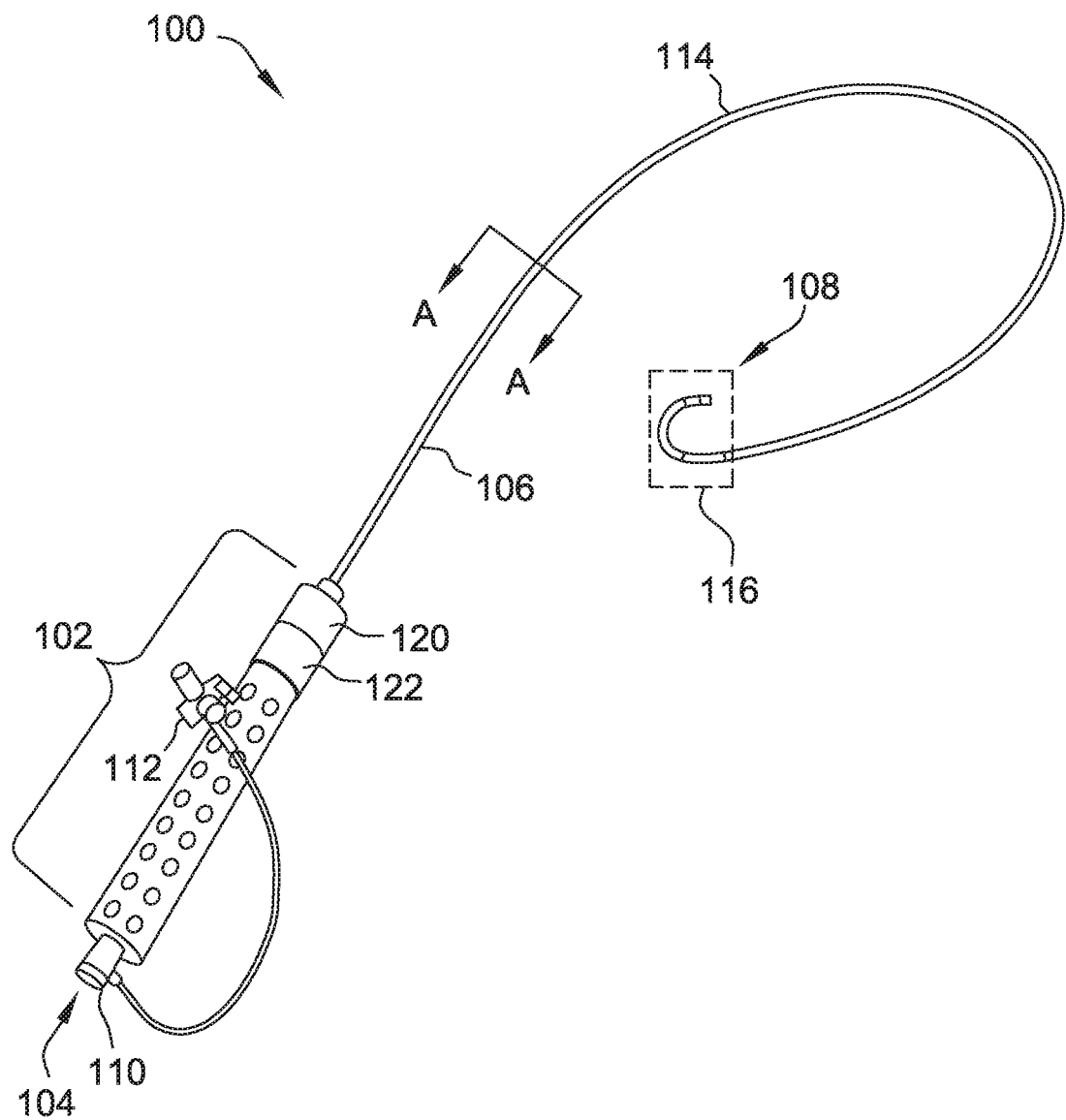
FIG. 1 is a perspective view of one embodiment of a steerable introducer.

Steerable introducers may include pull wires extending along a length of the introducer's steerable sheath from a proximal end of the sheath to a distal end of the sheath. As used herein, "proximal" refers to a direction toward the end of the introducer or sheath near the clinician and "distal" refers to a direction away from the clinician and (generally) inside the body of a patient. A pair of pull wires is positioned on opposite sides of the steerable sheath and each pull wire runs from the proximal end to the distal end of the steerable sheath. In use, one of the pull wires is shortened (e.g., pulled toward the proximal end of the steerable introducer) to place it under tension to cause a deflectable portion at the distal end of the steerable sheath to deflect in the direction of the tensioned pull wire in a plane containing the paired pull wires. To steer the distal end of the steerable sheath in a direction outside of the plane containing the paired pull wires, the operator applies a torque to the introducer to cause the sheath to rotate along its central axis, effectively rotating the plane containing the paired pull wires. When such torque is applied when one of the pull wires is under tension, the pull wires are rotated around the deflected portion of the sheath. The pull wire that is not under tension will need to shorten as it is rotated from an outside of the deflected portion (e.g., from an outer radius of a curve) to an inside of the deflected portion (e.g., to an inner radius of the curve) or the deflected portion of the sheath will change its deflection. Similarly, the tensioned pull wire needs to lengthen as it is rotated by the torque from the inside of the deflected portion to the outside of the deflected portion to maintain the same deflection of the sheath. During such an application of torque to the steerable introducer, energy is stored in the pull wires as the rotation of the sheath attempts to force them to change their lengths. This stored energy may release suddenly, causing the distal end of the steerable shear to make a sudden, fast, and unpredictable movement, sometimes referred to as whipping. At other times, the stored energy may cause one or both of the pull wires to break, typically at their anchor points within the handle of the steerable introducer.

Moreover, some procedures and/or anatomical features utilize delivery of catheters or other elongate devices into/ onto an anatomical structure, such as the heart, where deflection into the second plane starts from the position of the first plane. In at least some single plane systems, applying torque to the steerable introducer to move the plane is insufficient to reach certain areas of the heart, such as hard to reach pulmonary veins. In most cases, the right inferior pulmonary vein (RIPV) clinical effectivity is the lowest of all pulmonary vein (PV) isolations. This is at least in part due to device approach and lack of optimal seating in the right side PV. There is evidence of delivery shortcomings of other devices, such as, for example, left atrial appendage (LAA) devices.

Accordingly, the present disclosure is directed to a steerable sheath including pull wires configured to permit the steerable sheath to be deflected in multiple planes without application of torque to the introducer, thereby enhancing steerability of the steerable sheath, reducing the likelihood of breaking the pull wires, and/or reducing the likelihood of whipping of the distal end of the steerable sheath.

The systems and methods described herein provide a steerable sheath having more than one pair of pull wires that extend along the length of the steerable sheath. Each pair of pull wires is positioned in a different plane through the steerable sheath than each other pair of pull wires. This allows the steerable sheath to be deflected in more than one plane, allowing for more precise steering of the sheath and reducing the need for the application of torque to steer the steerable sheath.

Although described herein with respect to a steerable sheath as part of a steerable introducer, the teachings of the present disclosure may be applied to other steerable shafts, and particularly to other steerable medical devices. For example, the pull wire arrangements described herein may be applied to steerable catheters and intracardiac echocardiography catheters.

Referring now to the Figures, FIG. 1 is a perspective view of a steerable introducer 100 according to one embodiment. Introducer 100 includes a handle assembly 102 at a proximal end 104 and a steerable sheath 106 extending to a distal end 108 of steerable introducer 100. Steerable sheath 106 is operably coupled to handle assembly 102, which assists in guiding or steering steerable sheath 106 during procedures. Introducer assembly 100 further includes a hub 110 operably connected to an inner lumen (not shown) within handle assembly 102 for insertion or delivery of catheter assemblies, fluids, or any other devices known to those of ordinary skill in the art. Optionally, introducer assembly 100 further includes a valve 112 operably connected to hub 110. Steerable sheath 106 includes a flexible, non-deflectable portion 114 and a deflectable portion 116. Non-deflectable portion 114 extends from handle assembly 102 to deflectable portion 116. Components within sheath 106 (discussed below) in non-deflectable portion 114 and deflectable portion 116 may also be referred to as having corresponding non-deflectable and/or deflectable portions. Additional details of the construction and operation of a handle suitable for use as handle assembly 102 are described in U.S. Pat. No. 7,691,095, which is incorporated herein by reference in its entirety. In other embodiments, any other handle suitable for operating steerable sheath 106 may be used as handle assembly 102.

Deflectable portion 116 is configured to be controllably deflectable by an operator of introducer 100 using pull wires (not shown in FIG. 1) extending through steerable sheath 106 from deflectable portion 116 to handle assembly 102. The example embodiment includes four pull wires grouped in two pairs. Each pair of pull wires lies in a different plane than the other pair of pull wires. The two planes containing the two pairs of pull wires are orthogonal to each other in the example embodiment. In other embodiments, more than two pairs of pull wires may be included and/or the pairs of pull wires may be positioned in planes that are not orthogonal to each other.

Each pair of pull wires is operatively coupled to an actuator in handle assembly 102. A first actuator 120 controls a first pair of two pull wires that are positioned opposite one another along steerable sheath 106, and a second actuator 122 controls the remaining pair of two pull wires that are also positioned opposite one another along steerable sheath 106 and orthogonal to the first set of pull wires. While the actuators may be any type of actuator (e.g., rocker arms, rotational knobs, levers, slides, buttons, etc.), the illustrated embodiment utilizes two actuators 120 and 122 that are rotatable about the longitudinal axis of the steerable sheath 106.

Figure 2:
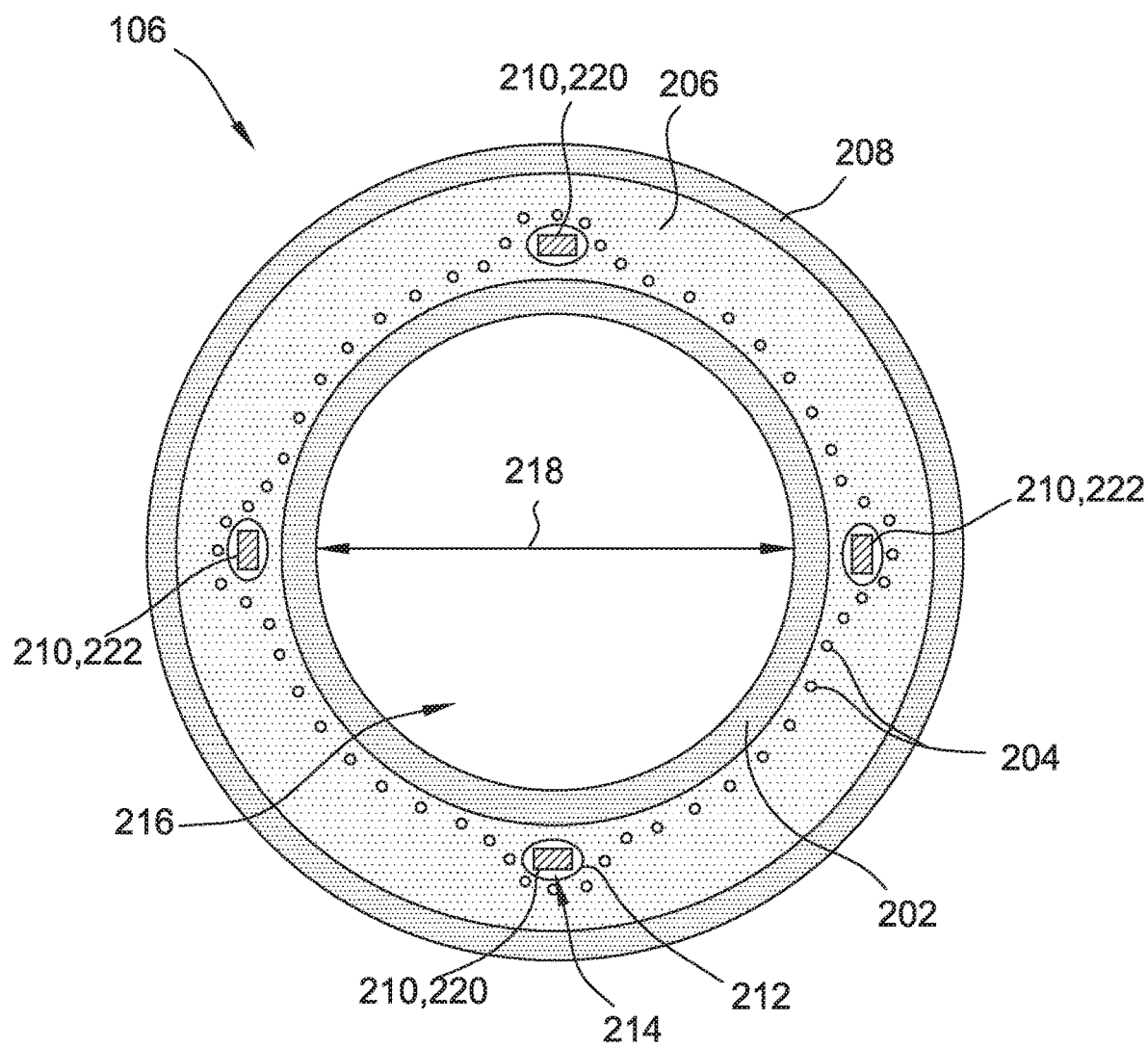
FIG. 2 is a cross section of a steerable sheath of the assembly shown in FIG. 1.
Figure 3:
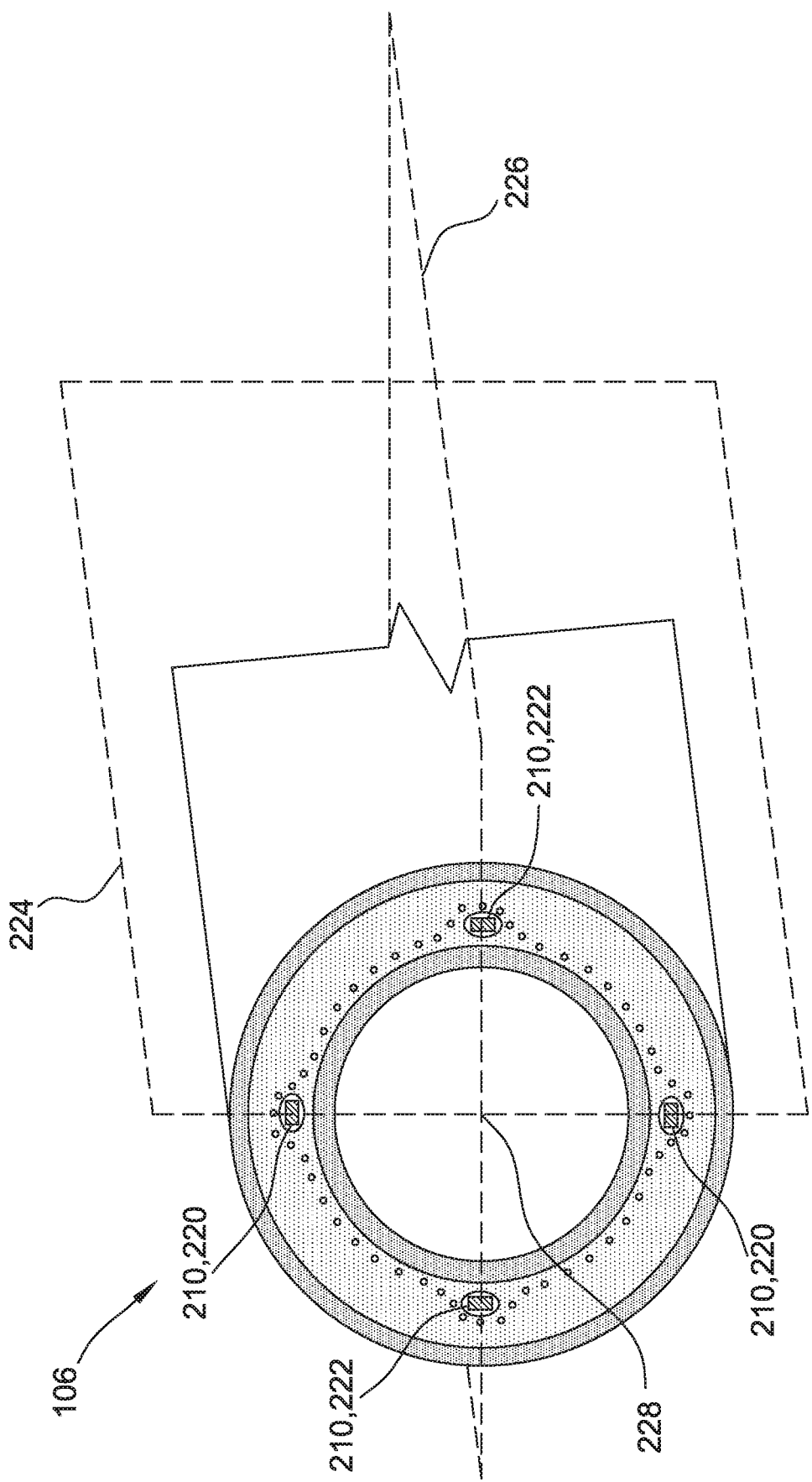
FIG. 3 is a an isometric view of the steerable sheath shown in FIG. 2.

FIG. 2 is a cross-sectional view of steerable sheath 106 taken along the line A-A shown in FIG. 1. FIG. 3 is an isometric view of steerable sheath 106 shown in FIG. 2. With reference initially to FIG. 2, steerable sheath 106 is comprised of a tubular inner liner 202 (also sometimes referred to as an "inner jacket"), a torque transfer layer 204, an outer sheath 206, a heat shrink layer 208 (also sometimes referred to as an "outer layer"), and pull wires 210. In other embodiments, the components of steerable sheath 106 may have different positions relative to each other component. For example, torque transfer layer 204 may be positioned radially inward of pull wires 210. In some embodiments, pull wires 210 are positioned directly adjacent inner liner 202. Heat shrink layer 208 is removed from steerable sheath 106 after the reflow process Steerable sheath 106 is manufactured using a reflow bonding process. Reflow bonding processes suitable for forming steerable sheath 106 are described in U.S. Pat. Nos. 7,914,515 and 8,734,699, which are incorporated herein by reference in their entireties. In other embodiments, any other suitable method for manufacturing steerable sheath 106 may be used.

In the example embodiment, pull wires 210 are flat wires. For purposes of this disclosure, a "flat wire" refers to a wire that is characterized by a cross-section that, when measured along two orthogonal axes, is substantially flat. A flat wire typically has a rectangular cross section, though the cross section need not be perfectly rectangular. For example, the present disclosure contemplates that a cross section of the flat wire may be oval, provided that the overall cross section is generally flat. As the term is used herein, a wire may be properly characterized as a flat wire if it has a cross section that is measured x in one direction and at least 2x in a second direction generally orthogonal to the first direction. A wire whose cross section is substantially I-shaped may also be a flat wire if, generally, its height is substantially greater than its width at its widest measurement. In other embodiments, pull wires 210 are round wires or wires of any other shape suitable for use as described herein.

Pull wire 210 is preferably about 0.002" (0.0508 mm) by about 0.016" (0.4064 mm), and more preferably about 0.004" (0.1016 mm) by about 0.012" (0.3048 mm) or 0.016" (0.4064 mm). Pull wire 210 may be selected such that the ratio of the width to thickness is at least about 2:1.

In the example embodiment, pull wires 210 are stainless steel wires. In other embodiments, pull wires 210 may be made of any other suitable material, such as spring steel, Nitinol (nickel titanium alloy), or a nickel-cobalt base alloy. A suitable nickel-cobalt base alloy includes MP35N®, which is a registered trademark of SPS Technologies. Inc., of Jenkintown, Pa., USA.

In the example embodiment, pull wires 210 are encased inside another polymeric tubular member 212 forming a lumen 214 for housing the pull wire 210. Polymeric tubular member 212 need not be the same shape as the cross section of pull wire 210, but instead, may be round, oval, rectangular, or another like shape. Preferably, the polymeric tubular member 212 has a cross section that is not the same shape as a cross section of pull wire 210, in order to facilitate movement of pull wire 210 in the preformed tube. Polymeric tubular member 212 may be formed of PTFE, etched PTFE, polyether block amides (such as Pebax), nylon, other thermoplastic elastomers, or any other known material to one of ordinary skill in the art. Preferably, the polymeric tubular member 212 has a higher melting point than outer sheath 206 so that polymeric tubular member 212 will not melt when steerable sheath 106 is subjected to reflow melt processing. In other embodiments lumen 214 is not formed using polymeric tubular member 212. Rather, pull wires 210 may be covered with lubricious materials (not shown) before placement, including silicone and other lubricious materials, and lumen 214 may be formed by the presence of pull wires 210 during the reflow process.

In the example embodiments, the pull wires 210 include paired first pull wires 220 (sometimes referred to as a first pair of pull wires 210) and paired second pull wires 222 (sometimes referred to as a second pair of pull wires 210). With reference to FIG. 3, first pull wires 220 are positioned in a first plane 224 and second pull wires 222 are positioned in a second plane 226. In the example embodiment, first plane 224 and second plane 226 are orthogonal planes. Alternatively, first pull wires 220 and second pull wires 222 may be positioned in non-orthogonal planes. Deflectable portion 116 of steerable sheath 106 may be deflected in two directions in each of planes 224 and 226. For example, applying tension to one of first pull wires 220 causes deflectable portion 116 to deflect within first plane 224 in the direction of the tensioned first pull wire 220 (relative to a center 228). Applying tension to the other first pull wire 220 causes deflectable portion 116 to deflect within plane first 224 in the direction of the other first pull wire 220. Deflections in first plane 224 and second plane 226 may be applied together to cause a resultant deflection of steerable sheath in a different plane. For example, applying equal tension to one of first pull wires 220 and one of second pull wires 222 will cause a deflection of deflectable portion 116 to a point along a plane angled approximately forty-five degrees to first plane 224 and second plane 226. In other embodiments, more than two pairs of pull wires 210 may be used to provide a desired number of deflection directions for steerable sheath 106. For example, three pairs of pull wires 210 may be used, with each pair of pull wires 210 positioned in a plane sixty degrees from the planes of the other two pairs of pull wires.

Pull wires 210 are connected to at least one steering ring (not shown) typically located near the distal end 108 (shown in FIG. 1) of steerable introducer 100. The proximal ends of pull wires 210 are operably connected to actuators 120 and 122 by connection to a steering mechanism (not shown) in handle 102 allowing for manipulation, or steering, of steerable sheath 106 during use. One pair of pull wires (e.g., first pull wires 220) is coupled to actuator 120, while the other pair of pull wires (e.g., second pull wires 222) is coupled to actuator 122. Additional details of the construction and operation of steering rings and steering mechanisms suitable for use in steerable introducer 100 are described in U.S. Patent Application Publication No. US2007/0299424, and U.S. Pat. Nos. 7,691,095, 7,914,515 and 8,734,699, each of which is incorporated herein by reference in its entirety.

Referring again to FIG. 2, inner liner 202 is preferably a polymeric material, such as polytetrafluoroethylene (PTFE) or etched PTFE. Inner liner 202 may also be made of other melt processing polymers, including, without limitation, polyether block amides, nylon and other thermoplastic elastomers. Once such elastomer is Pebax® made by Arkema, Inc. Pebax of various durometers may also be used, including without limitation, Pebax 30D to Pebax 70D. In a preferred embodiment, inner liner 202 is made of a material with a melting temperature higher than outer sheath 206 such that inner liner 202 will withstand the melt processing of the outer sheath 206.

Inner liner 202 defines a lumen 216 therethrough for receiving an elongate medical device, such as a catheter. Lumen 216 preferably has a diameter 218 of at least about 6 French, more preferably of at least about 7 French, and most preferably of between about 10 French and about 24 French. However, in some embodiments, it is contemplated that lumen 216 may have a diameter 218 of up to about 32 French or more, such as between about 7 French and about 32 French.

Torque transfer layer 204 is disposed between the inner liner 202 and the heat shrink layer 208, and more preferably between the outer sheath 206 and the inner liner 202. The torque transfer layer 204 may be made of stainless steel (e.g., 304 stainless steel or 316 stainless steel) wire or other acceptable materials known to those of ordinary skill in the art. The torque transfer layer 204 is preferably formed of a braided wire assembly comprised of flat wires, preferably stainless steel wires including, for example, high tensile stainless steel wires. The torque transfer layer 204 may be formed in any number of known braid patterns, including one-over-one (involving at least two wires) or two-over-two (involving at least four wires) crossover patterns. For lumen diameters of at least about 6 French, braided flat wires of at least about 0.003" thick by at least about 0.007" wide may be used. In general, the individual wires have a ratio of width to the thickness of at least about 2:1, including, for example, 2:1 to 5:1. Flat wires of about 0.004" (0.1016 mm) thick by about 0.012" (0.3048 mm) wide and of about 0.004" (0.1016 mm) thick by about 0.020" (0.508 mm) wide have also been braided with success to form torque transfer layers of superior performance.

Outer sheath 206 is preferably either an extruded Pebax or PTFE tubing. The melt-processing polymer of outer sheath 206 occupies a plurality of voids of the wire mesh in the torque transfer layer. Outer sheath 206 may also be made of other melt processing polymers, including, without limitation, etched PTFE, polyether block amides, nylon and other thermoplastic elastomers, at varying durometers. Outer sheath 206 may also comprise more than one layer, including, for example, two or more tubes of a melt processing polymer. Alternatively, outer sheath 206 may be comprised of varying segments (not shown) differing in hardness and/or material along the length of steerable sheath 106 and being reflow bonded together. Varying the sheath composition in this manner provides the additional benefit of adjusting flexibility, torqueability, and pushability at various points along steerable sheath 106.

Figure 4A:
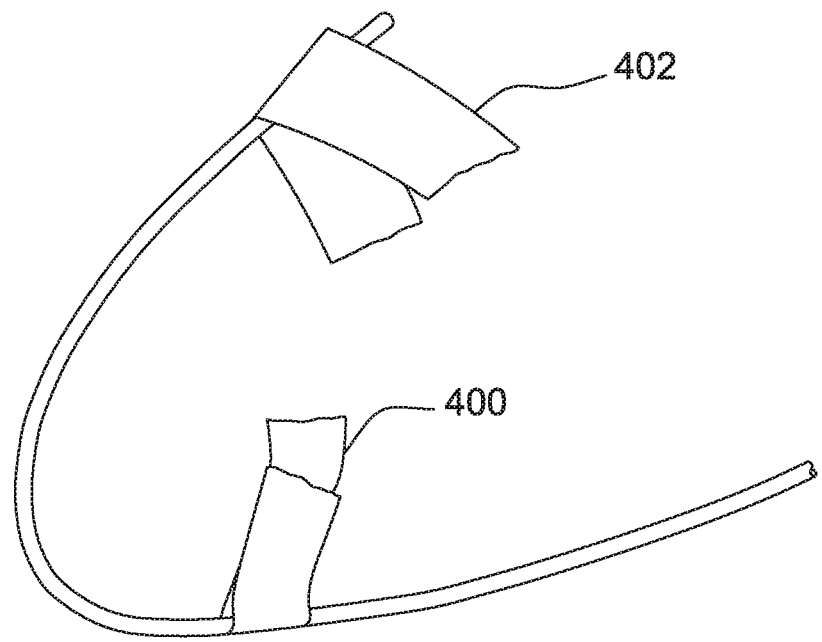
FIGS. 4A-4D are isometric views of a distal end of the steerable introducer shown in FIG. 1 as the distal end is deflected in two planes.

FIGS. 4A, 4B, 4C, and 4D illustrate a representative progression of deflections in steerable sheath 106. FIG. 4A shows a first deflection of steerable sheath 106. Steerable sheath 106 is deflected in a first plane, as depicted by a first plane flag 400 and a second plane flag 402 being substantially in the same plane. Steerable sheath 106 is deflected to the position shown in FIG. 4A by applying tension to one of first pull wires 220 using actuator 120.

Figure 4B:
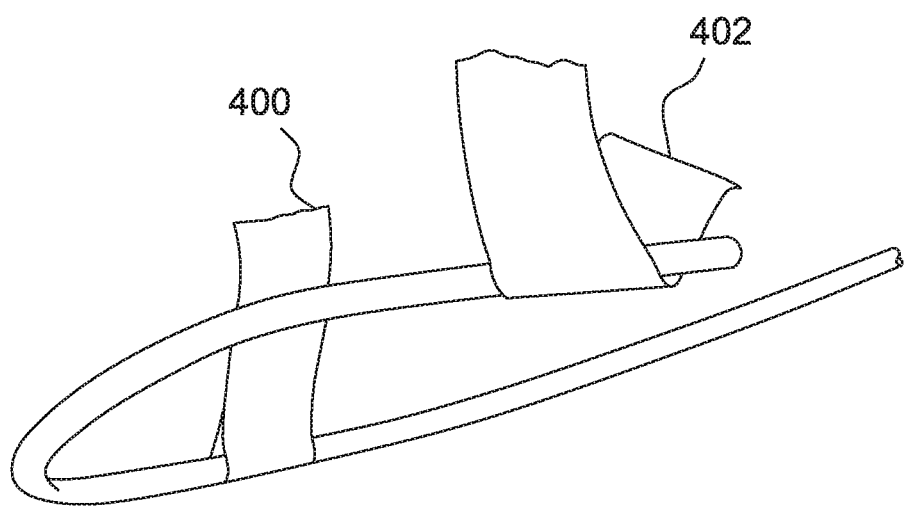

FIG. 4B shows a further progression of the collective deflection, depicting a second deflection from the first deflection, such that there are two planes of deflection as depicted by first plane flag 400 remaining in the first plane, and second plane flag 402 moving to a second plane as actuator 122 is actuated to apply tension to one of second pull wires 222. In this manner, coordinated manipulation of the actuators 120 and 122 can cause the steerable sheath 106 to be manipulated to virtually any desired position within the range of the collective actuations.

Figure 4C:
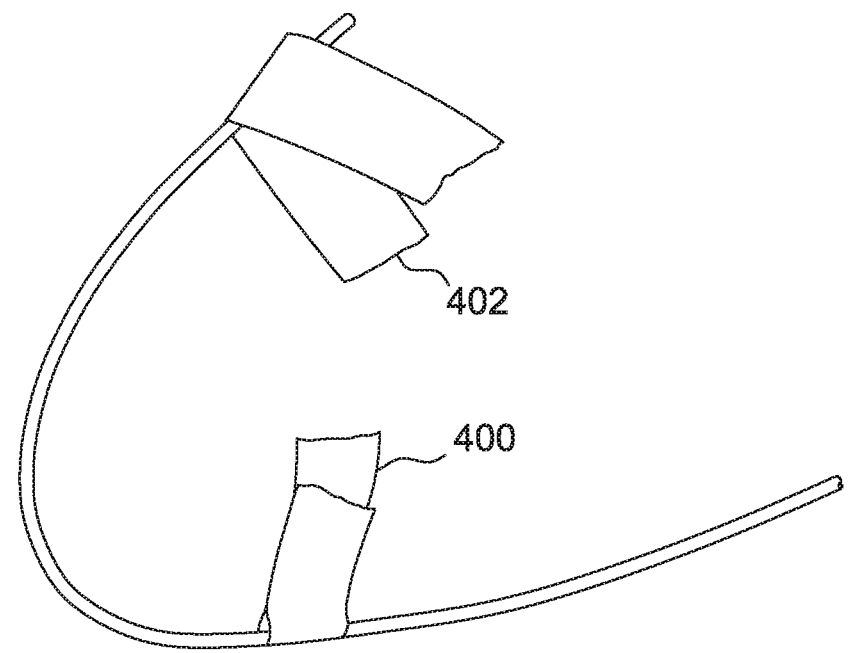

FIG. 4C depicts steerable sheath 106 returned to its original, single plane position (by reducing tension on the second pull wire 222 that was tensioned in FIG. 4B), where the first and second plane flags 400, 402 are again substantially in a single plane.

Figure 4D:
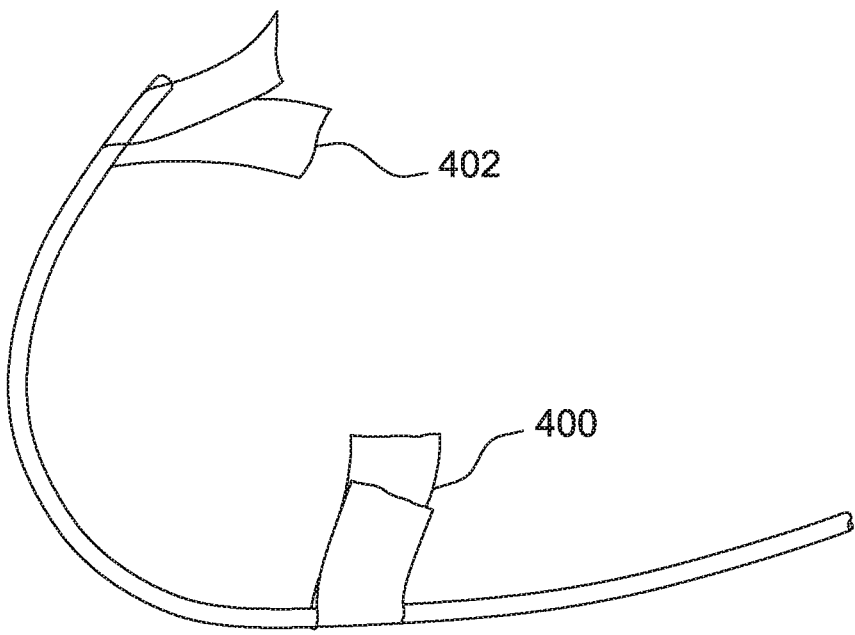
Figure 5A:
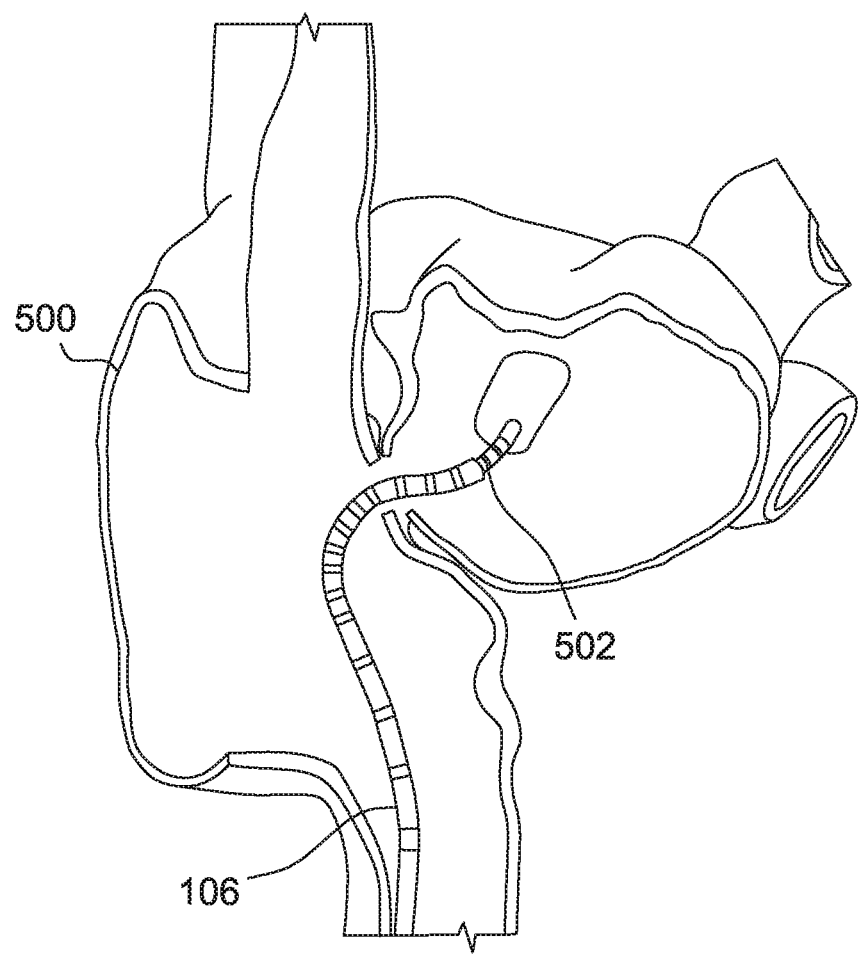
FIGS. 5A-5D are views of a human heart model with the distal end of the steerable introducer positioned within the heart model to access different target cardiac anatomical locations.
Figure 5B:
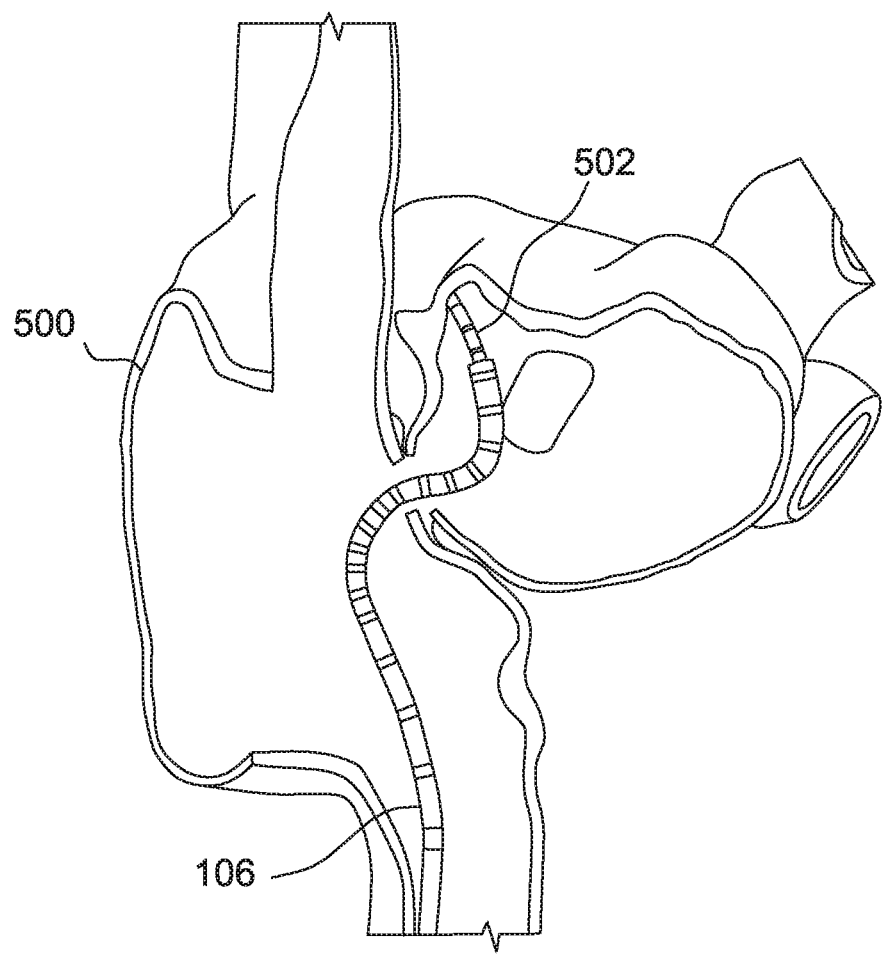
Figure 5C:
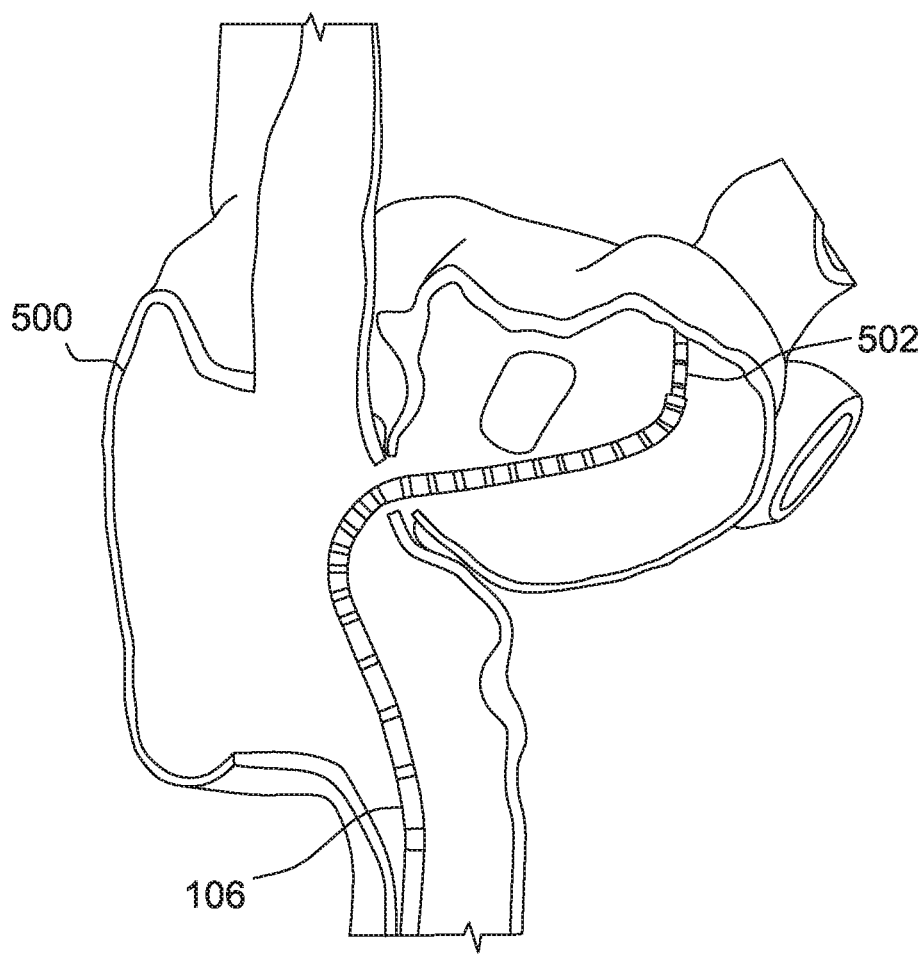
Figure 5D:
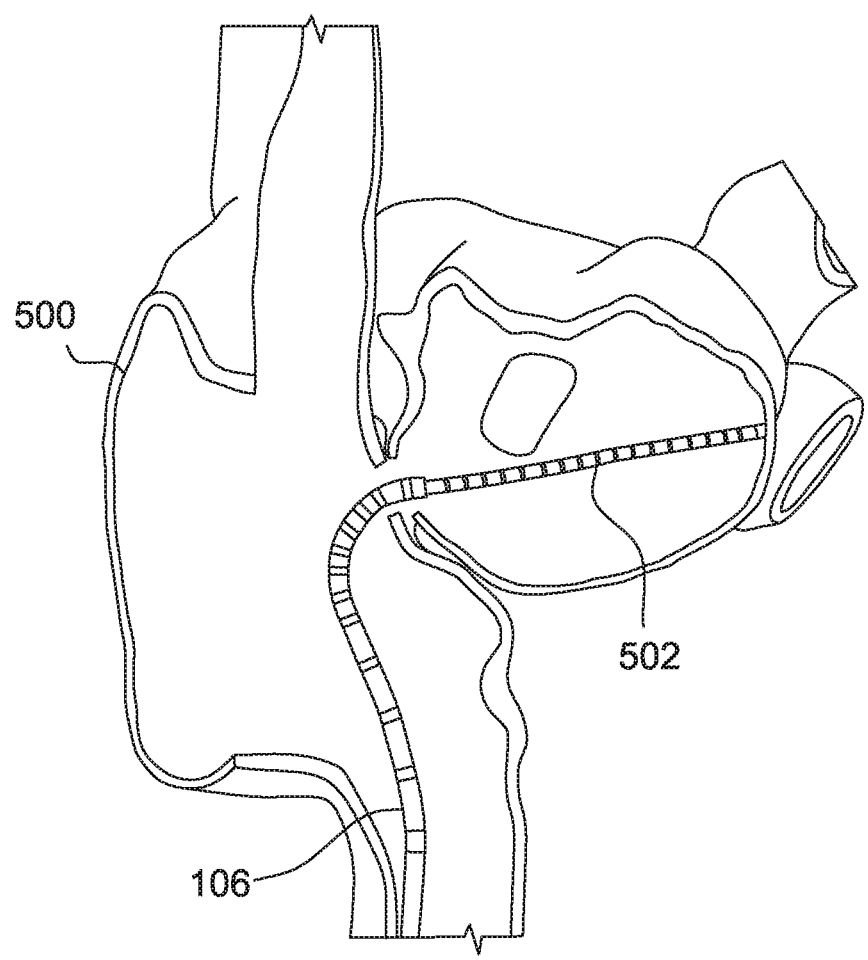

FIG. 4D shows a still further progression of the collective deflection, depicting a third deflection relative to the first deflection. In this deflection, there are two planes of deflection as seen by first plane flag 400 remaining in the first plane, and second plane flag 402 moving to a third plane through actuation of actuator 122 to increase tension on the second pull wire 222 that was not tensioned in FIG. 4B.

In this example, the first plane remains the same in FIGS. 4A-D, while the second plane rotates relative to the first plane from the position of FIG. 4A, to the position of FIG. 4B, to the position of FIG. 4C, and finally to the position of FIG. 4D.

FIGS. 5A-5D illustrate a human heart model 500, with various multi-plane deflections of steerable sheath 106 shown. As shown, a catheter 502 passing through lumen 216 of steerable sheath 106 is enabled to access various targeted cardiac anatomical positions.

Using deflectability in multiple planes, manipulation of multiple actuators of the disclosed steerable introducers enables distal end positioning between the intersecting planes, such that the distal portion can access any position along or between the intersecting planes within the reach of the deflecting distal end. In this manner, the distal end of the introducer can access virtually any position within a three-dimensional area surrounding a neutral-positioned (e.g., undeflected) distal end of the introducer.

It should also be noted that general accessibility instructions can be provided to reach a desired anatomical structure. For example, when in the left atrium at a known starting point, the first actuator may be actuated by a known amount, and the second actuator may subsequently be actuated by a known amount, to ultimately point in the vicinity of a particular target location. In this manner, given a known initial position of the introducer device, repeatable actuator control manipulations can direct the distal portion of the introducer at or near the target location.

Thus, the multi-plane introducers or other delivery devices described herein enable various types of delivered medical devices to be better positioned for diagnostics or therapy. In one embodiment, the device delivered via the lumen(s) of the multi-plane introducer is an electrophysiology diagnostic or therapy device. In more particular embodiments, the delivered devices are electrophysiology therapy devices, such as endocardial ablation catheters. Representative examples of such ablation catheters include radio frequency (RF) ablation devices, direct current ablation devices (e.g., electroporation devices), cryotherapy devices, heated liquid devices, ultrasound devices, etc. The delivered ablation catheters can have various ablation structures, such as linear catheter structures, loop or helical catheter structures, balloon catheter structures, multiple spline catheter structures, etc. For example, in one particular representative embodiment, the multi-plane introducer as described herein provides a lumen to guide a loop catheter to a cardiac structure, such as to provide a multi-electrode loop catheter providing DC/electroporation current to a structure such as a pulmonary vein to create targeted lesions in the cardiac tissue.

In yet other embodiments, the multi-plane introducer may assist in the delivery of other structures, such as cardiac occlusion devices, heart valves, leads, guidewires, transseptal access devices, etc. The recited devices are described for purposes of example only, as other devices may be delivered by the multi-plane introducers described herein.

Although a number embodiments of this disclosure have been described above with a certain degree of particularity, those skilled in the art could make numerous alterations to the disclosed embodiments without departing from the spirit or scope of the disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A steerable introducer having a proximal end and a distal end, the steerable introducer comprising:
    a steerable sheath having a proximal end and a distal end, the steerable sheath comprising:
        an outer layer extending from the proximal end to the distal end of the steerable sheath;
        an inner liner disposed within the outer layer and extending from the proximal end to the distal end of the steerable sheath;

a first pair of pull wires disposed between the inner liner and the outer layer and extending from the proximal end to the distal end of the steerable sheath; and a second pair of pull wires disposed between the inner liner and the outer layer and extending from the proximal end to the distal end of the steerable sheath, and a handle disposed at the proximal end of the steerable introducer, the handle comprising:
a first actuator operatively coupled to the first pair of pull wires; and
a second actuator operatively coupled to the second pair of pull wires,
wherein the first actuator is configured to selectively tension the first pair of pull wires to cause a deflectable portion of the steerable sheath to deflect within a first plane, and the second actuator is configured to selectively tension the second pair of pull wires to cause the deflectable portion of the steerable sheath to deflect within a second plane.

2. The steerable introducer of claim 1, wherein the first pair of pull wires is disposed in the first plane, the second pair of pull wires is disposed in the second plane, and the first plane is substantially orthogonal to the second plane.

3. The steerable introducer of claim 1, wherein the handle is operatively coupled to the proximal end of the steerable sheath.

4. The steerable introducer of claim 1, wherein the first pair of pull wires and the second pair of pull wires comprise flat wire.

5. The steerable introducer of claim 1, wherein the first pair of pull wires and the second pair of pull wires are stainless steel pull wires.

6. The steerable introducer of claim 1, wherein the inner liner defines a lumen configured to receive an elongate medical device.

7. A method of producing a steerable introducer comprising:
positioning a first pair of pull wires adjacent an inner liner of a steerable sheath, the first pair of pull wires extending from a proximal end of the steerable sheath to a distal end of the steerable sheath;
positioning a second pair of pull wires adjacent the inner liner of the steerable sheath, the second pair of pull wires extending from the proximal end of the steerable sheath to the distal end of the steerable sheath;
operatively coupling the first pair of pull wires to a first actuator such that selectively tensioning the first pair of pull wires, using the first actuator, causes a deflectable portion of the steerable sheath to deflect within a first plane; and
operatively coupling the second pair of pull wires to a second actuator such that selectively tensioning the second pair of pull wires, using the second actuator, causes the deflectable portion of the steerable sheath to deflect within a second plane.

8. The method of claim 7, wherein positioning the first pair of pull wires comprises positioning the first pair of pull wires in the first plane, and positioning the second pair of pull wires comprises positioning the second pair of pull wires in the second plane substantially orthogonal to the first plane.

9. The method of claim 7, further comprising:
operatively coupling a handle to the proximal end of the steerable sheath, wherein the handle includes the first and second actuators.

10. The method of claim 7, wherein positioning the first pair of pull wires comprises positioning a first pair of flat wire pull wires, and positioning the second pair of pull wires comprises positioning a second pair of flat wire pull wires.

11. The method of claim 7, wherein positioning the first pair of pull wires comprises positioning a first pair of stainless steel pull wires, and positioning the second pair of pull wires comprises positioning a second pair of stainless steel pull wires.

* * * * *